Figure 1:
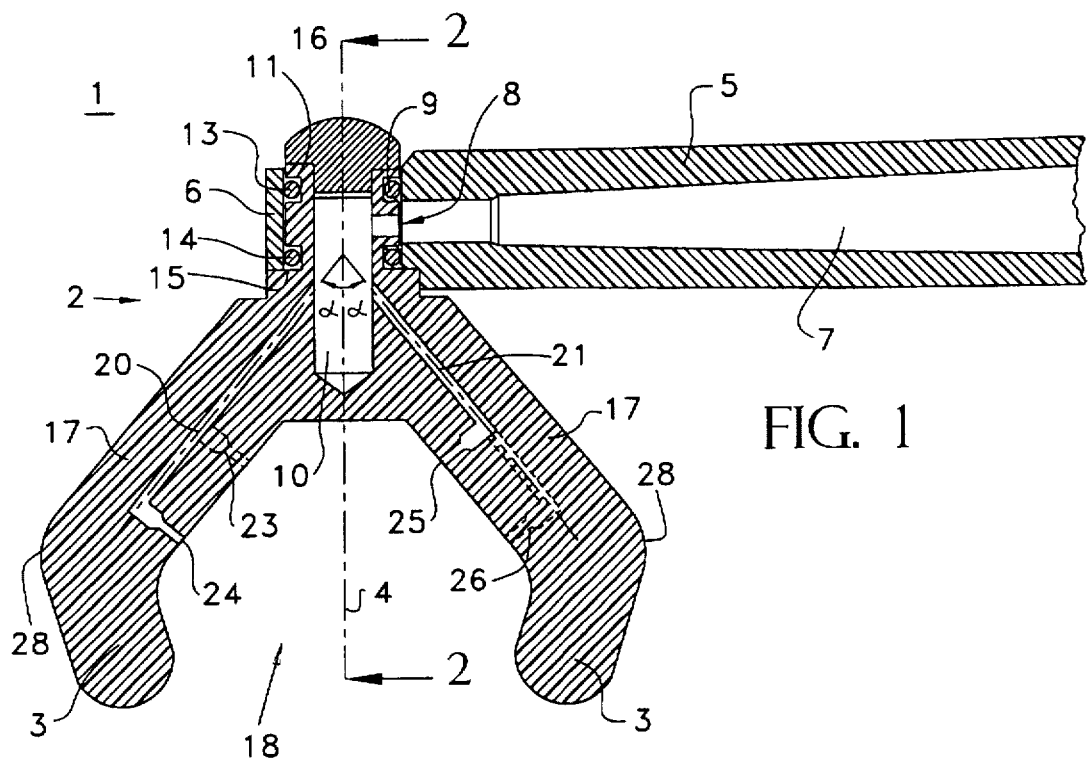

United States Patent

Saxer et al.

Patent Number: 5,800,367
Date of Patent: Sep. 1, 1998

[54] ORAL IRRIGATOR WITH A STIRRUP-SHAPED NOZZLE HOLDER

[75] Inventors: Ulrich P. Saxer, Zürich; Franz Fischer, Triengen, both of Switzerland

[73] Assignee: TRISA Bürstenfabrik AG Triengen

[21] Appl. No.: 722,209

[22] PCT Filed: Dec. 20, 1995

[86] PCT No.: PCT/CH95/00302

§ 371 Date: Oct. 16, 1996

§ 102(e) Date: Oct. 16, 1996

[87] PCT Pub. No.: WO96/25121

PCT Pub. Date: Aug. 22, 1996

[30] Foreign Application Priority Data

Feb. 17, 1995 [CH] Switzerland .................. 475/95

[51] Int. Cl.⁶ .................................................. A61C 15/00
[52] U.S. Cl. ........................................ 601/164; 433/80
[58] Field of Search ............................. 433/80; 601/164, 601/165, 163

[56] References Cited

U.S. PATENT DOCUMENTS

| | | |
|---|---|---|
| 1,500,107 | 7/1924 | Chandler ............................... 433/80 |
| 3,379,192 | 4/1968 | Warren, Jr. ............................ 601/164 |
| 3,489,141 | 1/1970 | Warren, Jr. ............................ 601/164 |
| 4,106,501 | 8/1978 | Ozbey et al. ........................... 433/80 |
| 4,611,992 | 9/1986 | Lokken .................................. 433/80 |
| 4,991,570 | 2/1991 | Bullard ................................... 433/91 |
| 5,360,025 | 11/1994 | Klinkhammer ....................... 15/167.1 |
| 5,443,386 | 8/1995 | Viskup ................................... 601/164 |

FOREIGN PATENT DOCUMENTS 42 08 664  9/1923  Germany .
365178  12/1962  Switzerland .

*Primary Examiner*—John J. Wilson
*Attorney, Agent, or Firm*—Duane, Morris & Heckscher LLP

[57] ABSTRACT

An oral irrigator (1), with a stirrup-shaped nozzle holder (2) which encloses the teeth on both sides via two branches (3), is described. Nozzle openings (23 to 26) are arranged on the inner side of the branches (3) and are oriented at an acute angle ($\beta$) to the axis of rotation (4) towards the open end (18) of the nozzle holder (2), in order to direct the nozzle jets (32), in the direction of the root (37), onto the lateral surfaces of the teeth (33).

10 Claims, 3 Drawing Sheets

ORAL IRRIGATOR WITH A STIRRUP-SHAPED NOZZLE HOLDER

The invention relates to an oral irrigator with a stirrup-shaped nozzle holder.

An oral irrigator of this kind is known, for example, from DE-A-40 29 369, which irrigator has an approximately U-shaped nozzle head which forms a tunnel and which has forty spray nozzles arranged in four planes around the circumference of the U-arch. The end regions of the U-shaped nozzle head are drawn in the direction of the teeth so that these end surfaces are guided on the surfaces of the teeth. The nozzle head has a length of approximately 2 cm so that, as it is moved along the teeth, about two to three teeth are covered at the same time. The spray nozzles are arranged in such a way that the spray jets in the central region are directed perpendicular to the tooth surfaces, and the spray jets in the end regions are directed at an angle of 45°, and from the bottom upwards at an acute angle. This last spray direction is provided so that the spray jets strike the tooth surfaces away from the gum, in order to prevent food debris or the like from being washed into the gingival pockets.

Although the spray jets are formed separately from one another, it is not possible to prevent a large surge of water from occurring on the tooth surface. In addition, the nozzle head has to be manufactured with extremely high precision so as to be able to create the specified effect. With the large number of spray nozzles, the irrigating fluid has to be passed through these at high pressure in order to achieve adequate cleaning. A further disadvantage of this known design of the oral irrigator is that it is not really possible to prevent a fairly large quantity of irrigating fluid from accumulating in the mouth, with the result that this irrigating fluid has to be expectorated and the cleaning thus interrupted over and over again. The width of the nozzle head, enclosing about two to three teeth, also represents an impediment to the rotational mobility on the dental arch, with the result that completely satisfactory handling is not always ensured.

The object of the present invention is to improve an oral irrigator of the abovementioned type in such a way that an enhanced irrigating action on the teeth is achieved in conjunction with a simpler design of the oral irrigator of the abovementioned type.

The invention has the essential advantage that an enhanced cleaning and irrigating action can take place, and a nozzle holder shape better adapted anatomically to the teeth can be obtained, in conjunction with substantially fewer nozzle jets. A further advantage is that the quantity of irrigating fluid which accumulates is smaller, and the handling of the oral irrigator is in this way easier.

Figure 2:
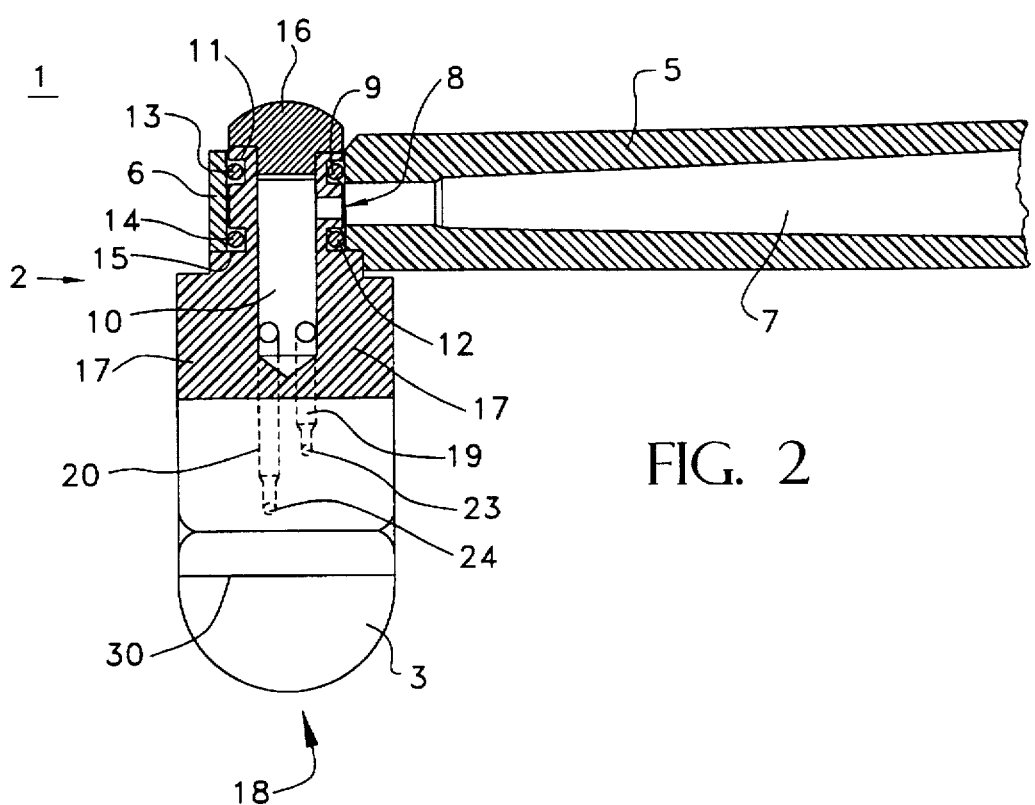
Figure 3:
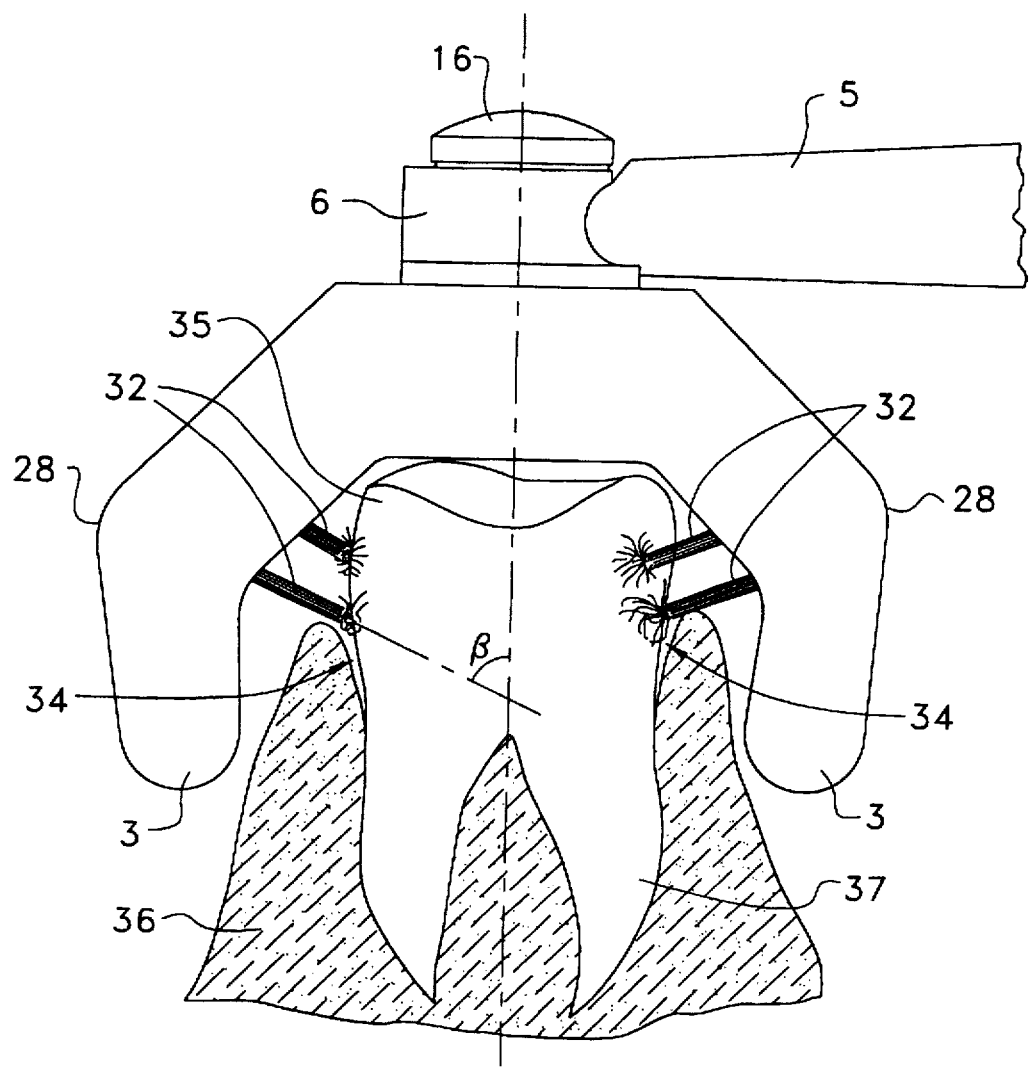
Figure 4:
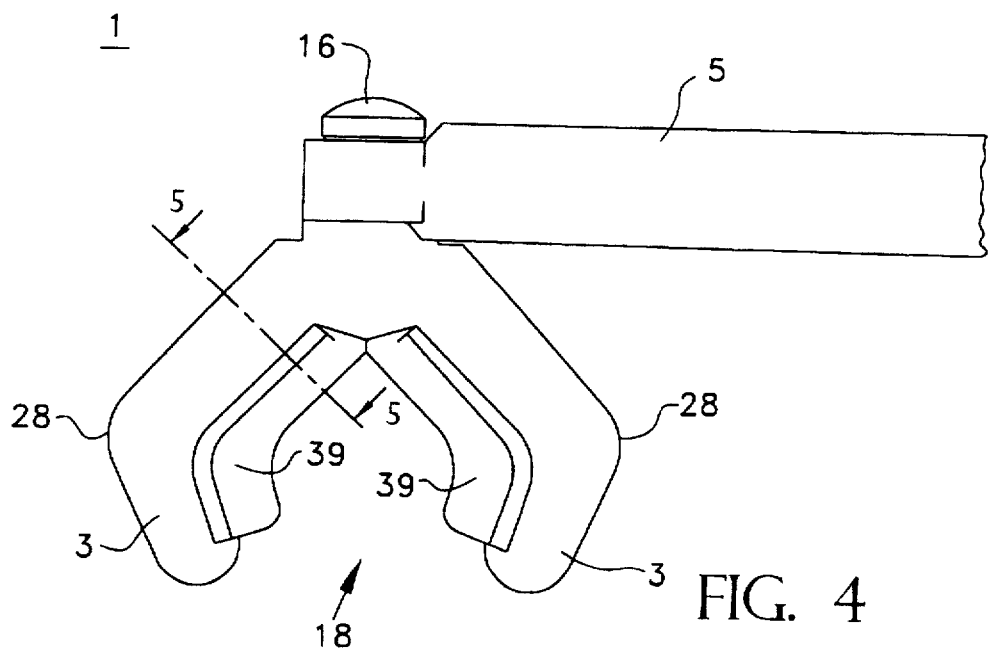
Figure 5:
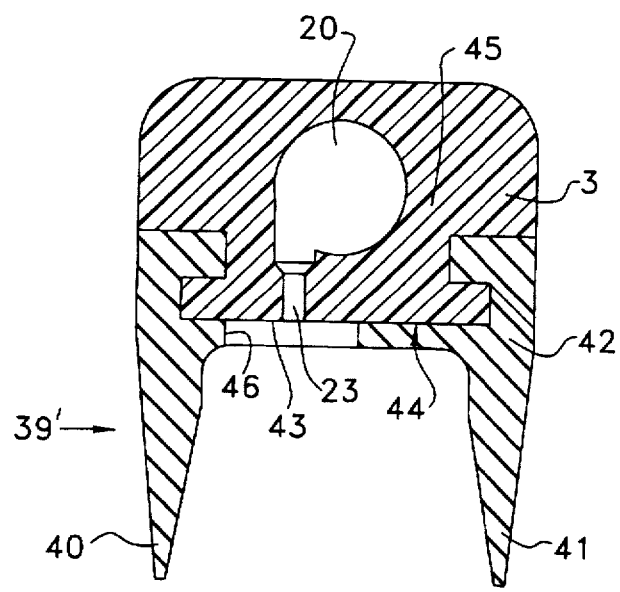

Further advantages are evident from the dependent claims and from the following description in which the invention is explained in greater detail on the basis of an exemplary embodiment represented in the diagrammatic drawings, in which:

FIG. 1 shows a cross-section through a nozzle holder of an oral irrigator,

FIG. 2 shows a cross-section through the same nozzle holder along the line A—A in FIG. 1, FIG. 3 shows a very diagrammatic sketch for the purpose of illustrating the use of the oral irrigator, FIG. 4 shows an alternative embodiment of the oral irrigator represented in FIG. 1, in horizontal projection, and FIG. 5 shows a cross-section through a branch of the oral irrigator in FIG. 4, along a section plane which is at right angles to the plane of projection and which is indicated by the line designated B—B in FIG. 4.

In the figures, the same references are used in each case for the same elements, and initial explanations apply equally to the other figures, unless otherwise stated.

FIGS. 1 and 2 show an oral irrigator 1 with a stirrup-shaped nozzle holder 2, which has two hook-shaped branches 3 of the same design. The nozzle holder 2 is connected to a tubular element 5 in a manner such that it can rotate about an axis of rotation 4. As can be seen, the tubular element 5 is designed with a channel 7 which tapers towards an annular end region or ring 6 and which opens into the circular-cylindrical hollow space 8 of the ring 6. The upper region 9 of the nozzle holder 2 is designed as a plug which has a blind bore 10 oriented towards the branches 3 on the axis of rotation 4. The plug 9 is provided on the outside with two parallel, circumferential grooves 11 and 12 into which an O-ring 13 and 14 made of rubber is in each case inserted for sealing with respect to the annular end region 6. The plug 9 has a shoulder 15 in the direction of the branches 3, which shoulder serves as a limit stop for the ring 6. The blind bore 10 is closed off at the top by a stopper 16. Starting from the blind bore 10, a short, straight delivery channel 19 and 21, respectively, and a long, straight delivery channel 20 and 22, respectively, are each provided in the upper region 17 of a branch 3, at an acute angle a with respect to the open end 18 of the nozzle holder 2. The delivery channels 19, 20 and 21, 22, respectively, in the same branch 3 are aligned approximately parallel. A nozzle opening 23 to 26 is provided at the end of each delivery channel 19 to 22, the nozzle axis of the opening being approximately transverse to the longitudinal direction of the respective delivery channel 19 to 22. The nozzle openings 23 to 26 are all of the same design and have a diameter of the discharge opening of approximately 0.5 mm. As can be seen in FIG. 1, the long delivery channel 20 and the short delivery channel 21 are arranged in the same plane, and likewise the delivery channels 19 and 22. The nozzle openings S 23, 24 and 25, 26, respectively, on the same branch 3 are arranged at a distance from each other which is sufficiently large to ensure that the approximately parallel and very slightly diverging nozzle jets do not influence one another. The nozzle jets in the same plane intersect one another, and their point of intersection lies in each case approximately at the level of the bend 28 of a branch 3.

The figure does not show the connection of the tubular element 5, designed as an attachment part, to a pressure pump via which the cleaning fluid is acted on intermittently by a high pressure, so that the nozzle jets are intermittently expelled simultaneously.

The width 30 of the branch 3 of the nozzle holder 2, as shown in FIG. 2, covers at most the average width of a premolar, i.e. is at most approximately 15 mm wide, preferably between approximately 10 and 12 mm.

The function of the oral irrigator 1 is now explained with reference to FIG. 3. As can be seen, the nozzle jets 32 are directed at an acute angle b to a tooth 33. The nozzle jets 32 are thus directed towards the gingival pockets 34 between the crown 35 and the gum 36. This is in complete contrast to the teaching of DE-A-40 29 369 which was mentioned in the introduction and according to which the lower spray jets are intended to spray upwards at an acute angle in order not to wash food debris or the like into the gingival pockets. Detailed investigations have shown, however, that any food debris getting into the gingival pockets 34 during irrigation and cleaning is very quickly flushed out by the gingival secretion. As irrigating fluid is delivered repeatedly, this fluid supports the gingival secretion, with the result that this natural action is additionally strengthened. The nozzle holder 2 is guided by its inner shape on the chewing surfaces and cutting surfaces of the teeth, and by the gum 36 in the region of the root 37, in which respect the small width of the nozzle holder 2 guarantees unproblematic guiding along any desired dental arch. The nozzle jets 32 moreover effect a slight massage of the gum 36 and the gingival margin, without exerting any kind of scrubbing action which could lead to damage to the gum. Thus, an effective reduction of gingivitis or inflammation of the gum can be achieved. In order to prevent the nozzle jets 32 from being obstructed in any way by splashes which bounce off the tooth surfaces acted on by the nozzle jets 32, the inner side of the branches 3 can be provided with bristles or covered with flock in the edge regions. These splashes are caught in this way and run off with the rest of the irrigating fluid. The guidance mentioned above is further improved by the inner surfaces of the nozzle holder 2 provided with bristles or covered with flock.

The design of the oral irrigator 1 as represented in the figures constitutes the preferred form. However, other configurations of the oral irrigator which afford an equally good action may be readily imagined. In particular, the delivery channels 19, 20 and 21, 22 can also be merged, and the nozzle openings 23, 24 and 25, 26 can be provided in each case at an acute angle to the plane through the merged delivery channels, these then being arranged in the same plane through the axis of rotation 4 of the nozzle holder 2. In such a case, the nozzle openings 19, 20 and 21, 22 are skew in relation to one another. In such a case, the nozzle axes of two nozzle openings each lying on opposite branches 3 are advantageously arranged in the same plane. More nozzle openings can also be provided, the maximum number having to be limited to ten in order to be able to exert a still sufficient irrigating and cleaning action.

An alternative embodiment of the oral irrigator 1 with a stirrup-shaped nozzle holder 2 is depicted in FIGS. 4 and 5, which oral irrigator has a rubber-elastic protector 39 on the inner side of the branches 3 facing the tooth surface, in order to afford a protective action against the jets of water bouncing back off the tooth surface. The exact design of this rubber-elastic protector 39 can be seen from FIG. 5, which represents a cross-section along the line B—B in FIG. 4 through a nozzle opening 23 not shown there (compare FIG. 1). The protector 39 consists of two lateral lips 40 and 41 which taper to a point and which are connected to each other via a support region 42. The support region 42 itself is provided with a T-shaped longitudinal groove 43 on the side facing the nozzle holder 2. The inner walls 44 of the branches 3 are designed with a T-shaped support element 45 in conformity with the longitudinal groove 43, as a result of which the rubber-elastic protector 39 can be pushed onto the branch 3. In the area of the nozzle opening 23 (compare also FIG. 1), a larger outlet opening 46 corresponding to this opening 23 is provided in the support region 42. During cleaning, the lips 40 and 41 brush over the tooth surface, so that an additional cleaning action is obtained. Silicone rubber, in particular vulcanized silicone rubber, has proven particularly expedient as a material for the lips 40 and 41, and thus for the protector 39, because damage to the gum can best be prevented by this means.

We claim:

1. An oral irrigator comprising a stirrup-shaped nozzle holder for enclosing a tooth on both sides via two branches and which on an inner side has nozzle openings and is connected in a rotatable manner to a tubular element, said nozzle openings being arranged in the branches, and the axes of the nozzle openings on a respective branch are oriented at an acute angle ($\beta$) to the axis of rotation and towards the open end of the nozzle holder, in order to direct the nozzle jets, in the direction of a root portion of said tooth, onto the lateral surfaces of said tooth wherein the width of said nozzle holder is no greater than about 15 mm, said irrigator providing a small volume of cleaning fluid which does not require expectoration to be effective.

2. The oral irrigator of claim 1, wherein the width of the nozzle holder is about 10 mm to about 15 mm.

3. The oral irrigator of claim 1, wherein each nozzle opening stems from a separate delivery channel.

4. The oral irrigator of claim 3, wherein said delivery channels are parallel on each of said branches.

5. The oral irrigator of claim 3, wherein two delivery channels lying on opposite branches lie in the same plane.

6. The oral irrigator of claim 1, wherein the nozzle openings of at least one branch open into a common delivery channel.

7. The oral irrigator of claim 6, where a plurality of nozzle axes of the nozzle openings on said one branch are skew in relation to one another.

8. The oral irrigator of claim 7, wherein the nozzle axes of at least two nozzle openings on opposite ones of said branches lie in the same plane.

9. The oral irrigator of claim 1 comprising less than 10 nozzle openings.

10. The oral irrigator of claim 1 wherein an inner side of said branches facing the tooth surface are provided with rubber-elastic protectors which have lips.

* * * * *